United States Patent
Birkbeck

(10) Patent No.: US 9,212,112 B1
(45) Date of Patent: Dec. 15, 2015

(54) PROCESS FOR THE PREPARATION OF BETA-SANTALOL

(71) Applicant: FIRMENICH SA, Geneva (CH)

(72) Inventor: Anthony A. Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/842,340

(22) Filed: Sep. 1, 2015

Related U.S. Application Data

(62) Division of application No. 14/125,876, filed as application No. PCT/EP2012/062615 on Jun. 28, 2012, now Pat. No. 9,156,770.

(60) Provisional application No. 61/503,244, filed on Jun. 30, 2011.

(30) Foreign Application Priority Data

Jun. 30, 2011 (EP) .................................... 11172038

(51) Int. Cl.
C07C 29/132 (2006.01)

(52) U.S. Cl.
CPC .................................... C07C 29/132 (2013.01)

(58) Field of Classification Search
None
See application file for complete search history.

(56) References Cited

U.S. PATENT DOCUMENTS

| 3,662,008 A | 5/1972 | Kretschmar et al. |
| 3,679,756 A | 7/1972 | Kretschmar et al. |

FOREIGN PATENT DOCUMENTS

| EP | 0 010 213 A2 | 4/1980 |
| EP | 2 119 714 A1 | 11/2009 |
| WO | 2006/120639 A2 | 11/2006 |
| WO | 2008/120175 A1 | 10/2008 |
| WO | 2009/141781 A1 | 11/2009 |

OTHER PUBLICATIONS

Brunke et al., "The Chemistry of Sandalwood Odour—A Review of the Last 10 Years," Rivista Italiana EPPOS, 49-82 (1997).
Cornish et al., "Homogeneous Catalysis. IV. Hydrosilylation of Cyclic or Linear Dienes Using Low-Valent Nickel Complexes and Related Experiments," Journal of Organometallic Chemistry, 132:133-148 (1977).
Ely et al., "Regio- and Stereoselective Ni-Catalyzed 1,4-Hydroboration of 1,3-Dienes: Access to Stereodefined (Z)-Allylboron Reagents and Derived Allylic Alcohols," J. Am. Chem. Soc., 132(8):2534-2535 (2010).
Fehr et al., "Enantioselective Synthesis of (-)-β-Santalol by a Copper-Catalyzed Enynol Cyclization-Fragmentation Reaction," Angew. Chem. Int. Ed. 48(30):7221-7223 (2009).
Fehr et al., "The Synthesis of (Z)-Trisubstituted Allylic Alcohols by the Selective 1,4-Hydrogenation of Dienol Esters: Improved Synthesis of (-)-β-Santalol," Chem. Eur. J., 17(4):1257-1260 (2011).
Krotz et al., "Total Syntheses of Sandalwood Fragrances: (Z)- and (E)-β-Santalol and Their Enantiomers, ent-β-Santalene," Tetrahedron: Asymmetry, 1(8):537-540 (1990).
Spangler et al., "3-Alkoxypropenals as Precursors in the Synthesis of Conjugated and Semiconjugated Polyenes: Methyl-Substituted Octa- and Nona-tetraenes," J. Chem. Soc., Perkin Trans. 1, 1203-1207 (1986).
Spangler et al., "A Convenient and Efficient Preparation of Conjugated and Nonconjugated Substituted Dienals from 3-Alkoxypropenals," Synthetic Communications, 15(5):371-376 (1985).
Takahashi et al., "New Method for the Introduction of a Carbon-Carbon Triple Bond at C-13 in PG Synthesis. A Stereocontrolled Synthesis of ZK 96 480," J. Org. Chem., 53:1227-1231 (1988).
Wu et al., "Iron-Catalyzed 1,4-Hydroboration of 1,3-Dienes," J. Am. Chem. Soc., 131(36):12915-12917 (2009).
Wu et al., "A Strategy for the Synthesis of Well-Defined Iron Catalysts and Application to Regioselective Diene Hydrosilylation," J. Am. Chem. Soc., 132(38):13214-13216 (2010).
International Search Report and Written Opinion, Appl. No. PCT/EP2012/062615, Aug. 28, 2012.
U.S. Appl. No. 14/125,876, Restriction Requirement, May 7, 2015.
U.S. Appl. No. 14/125,876, Non-Final Office Action, Jul. 14, 2015.
U.S. Appl. No. 14/125,876, Notice of Allowance, Jul. 28, 2015.

*Primary Examiner* — Karl J Puttlitz
(74) *Attorney, Agent, or Firm* — Winston & Strawn LLP

(57) ABSTRACT

The present invention concerns a process for the preparation of a compound of formula

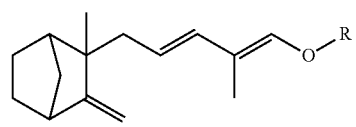

(I)

in the form of any one of its stereoisomers or mixtures thereof, wherein R represents a $C_1$-$C_7$ alkyl or alkenyl group, a $C_7$-$C_{10}$ benzyl group optionally substituted by one to three $C_{1-3}$ alkyl or alkoxy groups, a $C_1$-$C_7$ acyl group or an alkoxycarbonyl of formula $C(=O)OR'$, wherein R' is a $C_1$-$C_7$ alkyl group.

4 Claims, No Drawings

PROCESS FOR THE PREPARATION OF BETA-SANTALOL

CROSS-REFERENCE TO RELATED APPLICATIONS

This application is a division of U.S. patent application Ser. No. 14/125,876 filed on Dec. 12, 2013, which is a 371 filing of International application no. PCT/EP2012/062615 filed on Jun. 28, 2012, which claims the benefit of U.S. provisional application No. 61/503,244 filed on Jun. 30, 2011 and claims priority to European application no. 11172038.9 filed on Jun. 30, 2011, the entire contents of each of which are incorporated herein by reference thereto.

TECHNICAL FIELD

The present invention relates to the field of organic synthesis and more specifically it concerns a process for the preparation of a compound of formula

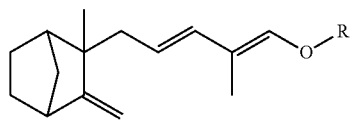

(I)

wherein R is as defined below, and said compound is in the form of any one of its stereoisomers or mixtures thereof. The invention also concerns the use of compound (I) for the synthesis of β-santalol or of derivatives thereof.

BACKGROUND

The compounds of formula (I) are useful starting materials for the preparation of β-santalol ((Z)-2-methyl-5-((1SR,2RS,4RS)-2-methyl-3-methylenebicyclo[2.2.1]heptan-2-yl)pent-2-en-1-ol, i.e. the exo isomer), and derivatives thereof, in a very short, effective and industrially feasible manner.

The β-santalol, and derivatives thereof, are well known and highly valued perfuming ingredients, some of which have particular relevance. Synthetic β-santalol is not commercially available at this time and it is only available from natural sources (Sandalwood sp. essential oils). β-santalol is present in East Indian Sandalwood Oil (*Santalum album*) at a typical level of 20-25% and is generally accepted as the principal odor vector for the fine creamy sandalwood character of the essential oil. The West Australian Sandalwood Oil (*Santalum spicatum.*) typically contains much less β-santalol, in the range of 3-8% of the essential oil, and as a result is a less appreciated oil.

The export of East Indian sandalwood and the distillation of the essential oil is under strict government control since *Santalum Album* has been classified by the Convention on International Trade in Endangered Species of Wild Fauna and Flora and International Union for Conservation of Nature Red list as vunerable and at risk of extinction.

Therefore, there is an urgent need for alternative syntheses to produce β-santalol and its derivatives.

To the best of our knowledge, all known syntheses are lengthy or require expensive starting materials and/or reagents or even steps which are too expensive for an industrial process or generate unacceptable quantities of waste (e.g. see Brunke at al., in Rivista Italiana EPPOS, 1997, 49).

In particular one may cite the following references, which are representative of the best examples of processes for the preparation of β-santalol:

- EP 10213: however said process, besides the fact that it is very long, requires many chlorinated intermediates (not optimal for a use in perfumery) and provides a very low overall yield for the preparation of an enal which still requires several steps to be converted into the desired product;
- A. Krotz et al, in *Tet.Asymm.*, 1990, 1, 537: a relatively short synthesis, however it requires expensive reducing reagents that are difficult to manipulate on large scale, expensive chiral auxillaries and two Wittig reactions, and then subsequent transformation of a ketone into the exo-methylene group;
- U.S. Pat. No. 3,662,008 and U.S. Pat. No. 3,679,756 (P&G) also describe the synthesis of β-santalol in low overall yield. This route is also dependent on a Wittig reaction to install the Z double bond and expensive reducing agents;
- WO2009/141781: reports a synthesis of some derivatives of formula (I), used as intermediates in the preparation of santalol; however said synthesis is long and still passes through the same key enal intermediate as described in EP 10213.

Thus, there is a need for improved processes for the preparation of β-santalol and these are now provided by the present invention.

SUMMARY OF THE INVENTION

The present invention provides a more industrial and efficient process for the preparation of β-santalol, and derivatives thereof. Indeed, the present invention shortens the overall process of preparation of the targeted compounds by allowing the three-step preparation of santalol from santene by creating a suitably functionalised side-chain moiety (with the correct configuration) together with the concomitant formation of the methylene function (without the mandatory need of a Wittig olefination or similar transformations) using a novel reaction without literature precedent.

It is well known in the literature that despite the epi-β-santalol being present in the natural East Indian sandalwood oil, it contributes little to the overall odor impact of the oil (REF). Thus, a selective synthesis of (Z)-β-santalol containing a minimum of epi-β-santalol, and a minimum of the (E)-β-santalol thus highly desirable.

The present invention also provides new compounds that are useful in this process, as well as the use of such compounds for the preparation of β-santalol.

DESCRIPTION OF THE INVENTION

The present invention relates to a process for the preparation of a compound of formula

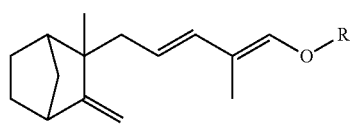

(I)

in the form of any one of its stereoisomers or mixtures thereof, wherein R represents a $C_1$-$C_{10}$ group of formula $CO(O)_v R^a$ wherein v=1 or 0, and $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

As will be shown further below, these compounds (I) are direct precursors of β-santalol (in particular (Z)-2-methyl-5-((1S,2R,4R)-2-methyl-3-methylene-bicyclo[2.2.1]heptan-2-yl)pent-2-en-1-ol).

A particular aspect of the present invention is a process for the preparation of a compound of formula

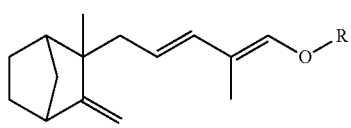

(I)

in the form of any one of its stereoisomers or mixtures thereof, and wherein R represents a $C_1$-$C_{10}$ group of formula $CO(O)_v R^a$ wherein v=1 or 0, and $R^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms;

by reacting together a compound of formula

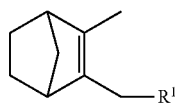

(II)

in the form of any one of its stereoisomers or mixtures thereof, and wherein $R^1$ represents a hydrogen atom or a $Si(R^2)_3$ or $B(OR^{2'})_2$ group, $R^2$ representing a $C_{1-4}$ alkyl or alkoxyl group and $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups;

with a compound of formula

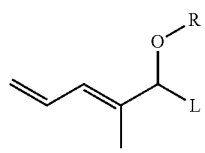

(III)

in the form of any one of its stereoisomers or mixtures thereof, and wherein R has the meaning defined in formula (I) and L represents a halogen atom or an OR group;

in the presence of 1) at least one Lewis acid selected amongst
   i) a metal salt of a an element of the group 2, 3, 4, 13 or of a 3 d element or of tin;
   ii) an alkyl aluminum chloride of formula $Al(R^4)_a Cl_{3-a}$, a representing 1 or 2 and $R^4$ representing $C_{1-10}$ alkyl or alkoxide group; and
   iii) a boron derivative of formula $BZ_3$, wherein Z represents a fluoride or a phenyl group optionally substituted, and anyone of its adduct with a $C_2$-$C_{10}$ ether or a $C_1$-$C_8$ carboxylic acid; and 2) optionally an additive selected amongst the group consisting of alkaline-earth hydroxide or oxide and of the compounds of formula $R^b COCl$, $ClSi(R^b)_3$, $R^b COOR^c$ or $(R^b\text{-}COO)_2 R^d$, $R^b$ representing a $C_{1-12}$ alkyl group or a phenyl group optionally substituted by one or two $C_{1-4}$ alkyl or alkoxyl group, and $R^c$ representing an alkaline metal cation or a $R^b CO$ acyl group, and $R^d$ representing an alkaline-earth metal cation.

The invention's process is, to the best of our knowledge, the first example of a Scriabine type reaction reported in the literature and using an alkene instead of an aromatic compound. It is also to our knowledge the first example of a Scriabine type reaction reported in the literature and using a diene compound of the type of formula (III).

The compound of formula (II) can be obtained according to *Chem Ber.*, 1955, 88, 407 (for santene, i.e. $R^1$ is a hydrogen atom).

The corresponding silyl ($R^1$=$Si(R^2)_3$) or boryl ($R^1$=$B(OR^{2'})_2$) compounds can be obtained by either 1,4 hydrosilylation, (see *J. Organometallic Chem.*, 1977, 132, 133, *J. Am.Chem. Soc.*, 2010, 132, 13214) or 1,4 hydroboration (see *J.Am.Chem.Soc.*, 2009, 131, 12915, or *J.Am.Chem. Soc.*, 2010, 132, 2534.) of the corresponding santadiene (see *Chem. Ber.*, 1955, 88, 407). Alternatively these same products can be obtained via mono functionalisation of santene via deprotonation with Lochmann-Schlosser base as described in *Chem. Ber.*, 1994, 127, 1401 and *Chem. Ber.*, 1994, 127, 2135 using the appropriate reagent.

According to any embodiment of the invention, and independently of the specific aspects, said $R^1$ group represent a hydrogen atom.

Alternatively said $R^1$ group represents a $Si(R^2)_3$, $R^2$ representing a $C_{1-4}$ alkyl or alkoxyl group, or a $B(OR^{2'})_2$ group, $R^{2'}$ representing, taken separately, a $C_{1-4}$ alkyl group or a or a phenyl group optionally substituted by one to three $C_{1-3}$ alkyl or alkoxy groups, or said $R^{2'}$, taken together, representing a $C_{2-6}$ alkanediyl group or a diphenyl or dinaphthyl group optionally substituted by one to three $C_{1-3}$ alkyl or alkoxy groups.

It is understood, by the skilled person that whenever said $R^1$ group does not represent a hydrogen atom, said compound (II) can be already in an optically active form and be an optimal starting material in view of obtaining an optically active β-santalol.

According to any embodiment of the invention, said compound (II) is triethyl(((1S,4S)-3-methylbicyclo[2.2.1]hept-2-en-2-yl)methyl)silane, 2,3-dimethylbicyclo[2.2.1]hept-2-ene (santene) or 4,4,5,5-tetramethyl-2-(((1S,4S)-3-methylbicyclo[2.2.1]hept-2-en-2-yl)methyl)-1,3,2-dioxaborolane. In particular, said compound (II) is 2,3-dimethylbicyclo[2.2.1]hept-2-ene (santene).

The compounds of formula (III), to the best of our knowledge are novel compounds. Therefore, a second object of the invention are the novel and useful compounds of formula (III)

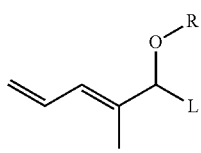

(III)

in the form of any one of its stereoisomers or mixtures thereof, and wherein R has the meaning defined in formula (I) and L represents a halogen atom or an OR group. In particular one may cite the ones wherein R is $C_{2-6}$ acyl group and L is an OR group or Cl. In particular one may cite the (E)-2-methylpenta-2,4-diene-1,1-diyl dicarboxylate, wherein by carboxylate it is meant a $C_{1-7}$, preferably a $C_{2-6}$, acyl group as defined above.

According to any embodiment of the invention, and independently of the specific aspects, said R group represents a $C_1$-$C_{10}$ alkoxycarbonyl group of formula $COOR^a$ or acyl group of formula $COR^a$ wherein, and $R^a$ is
- a phenyl or benzyl group optionally substituted by one or two alkyl, alkoxyl, carboxyl, acyl, amino or nitro groups; or
- a branched alkyl or alkenyl group comprising in the α position a tertiary or quaternary carbon atom and/or in the 13 position a quaternary carbon atom.

Alternatively, said R is a $C_2$-$C_{10}$ acyl or alkoxycarbonyl group. In particular said R group is a $C_4$-$C_7$ acyl group and $R^a$ is a branched alkyl group comprising in the α position a tertiary or quaternary carbon atom and/or in the 13 position a quaternary carbon atom.

For the sake of clarity, by the expression "α position" it is meant the usual meaning in the art, i.e. the carbon atom directly bound to the COO moiety of the group R. Similarly by the expression "β position" it is meant a carbon atom directly bound to the α position.

Specific examples of said R are, EtCO, $^i$PrCO, $^{sec}$BuCO, $^t$BuCH$_2$CO, $^t$BuCO or PhCH$_2$CO.

Some of the compound of formula (I) are new compounds.

According to any embodiment of the invention, and independently of the specific aspects, said L group represent a Cl or Br atom or represents a OR group as defined above.

The process for the preparation of a compound (I), according to the invention, requires a Lewis acid, which is used as catalyst for the Scriabine reaction.

The invention's process is carried out in the presence of a Lewis acid of various natures, inter alia a particular metal salt. According to any embodiment of the invention, and independently of the specific aspects, said metal salt is advantageously selected amongst the compounds formula $$(M^{n+})(X^-)_{n-m}(Y^-)_m$$

wherein m is an integer from 0 to (n−1), and
- n is 2 and M is Zn, Cu or an alkaline earth metal;
- n is 3 and M is a lanthanide, Sc, Fe, Al; or
- n is 4 and M is Sn, Ti or Zr;

each $X^-$ represents $Cl^-$, $Br^-$, $I^-$, a non-coordinating monoanion, $R^3SO_3^-$ wherein $R^3$ represents a chlorine or fluorine atom, or a $C_{1-3}$ hydrocarbon or perfluoro hydrocarbon, or a phenyl optionally substituted by one or two $C_{1-4}$ alkyl groups; each $Y^-$ represents a $C_{1-6}$ carboxylate or 1,3-diketonate when n is 2 or 3, or a $C_{1-6}$ alkoxylate when n is 3 or 4.

By the expression "weakly-coordinating monoanion" it is meant the usual meaning in the art, i.e. an monoanion which is weakly-coordinated or very weakly coordinated to the metal center. Typically such weakly-coordinating monoanion are the anions of acids HX having a p$K_a$ below 1. Non limiting examples of such non-coordinating monoanion are $ClO_4^-$, $BF_4^-$, $PF_6^-$, $SbCl_6^-$, $AsCl_6^-$, $SbF_6^-$, $AsF_6^-$ or $BR_4^-$, wherein R is a phenyl group optionally substituted by one to five groups such as halide atoms or methyl or $CF_3$ groups, and in particular are $PF_6^-$ or $BF_4^-$.

According to any embodiment of the invention, and independently of the specific aspects, said Lewis acid is selected amongst the compounds formula $$(M^{n+})(X^-)_{n-m}(Y^-)_m$$

wherein m is an integer from 0 to (n−1), and
- n is 2 and M is Zn or Mg, Cu;
- n is 3 and M is Fe, Ce, Al; or
- n is 4 and M is Sn;

each $X^-$ represents $Cl^-$, $Br^-$, $I^-$, $PF_6^-$, $BF_4^-$, $R^3SO_3^-$ wherein $R^3$ represents a $C_{1-3}$ hydrocarbon or perfluoro hydrocarbon or a phenyl optionally substituted by one or two $C_{1-4}$ alkyl groups;
each $Y^-$ represents a $C_{1-6}$ carboxylate or 1,3-diketonate when n is 2 or 3, or a $C_{1-6}$ alkoxylate when n is 3 or 4.

According to any embodiment of the invention, said $X^-$ represents $Cl^-$, $Br^-$, $I^-$, $CF_3SO_3^-$ or $BF_4^-$ or $PF_6^-$.

According to any embodiment of the invention, when $X^-$ represents a halide, in particular $Cl^-$ or $I^-$, then $M^{n+}$ is $M^{4+}$, $Fe^{3+}$ or $Zn^{2+}$; alternatively when $X^-$ represents a non-coordinating monoanion or $R^3SO_3^-$, in particular $CF_3SO^-$ (OTf), then $M^{n+}$ is $M^{3+}$ or $M^{2+}$.

It is understood by a person skilled in the art that the nature of X may depend on the redox potential of the anions X (in particular when said anion X is an halogen) and the redox potential of the metal cation.

According to any embodiment of the invention, said $Y^-$ represents a $C_{1-6}$ carboxylate when n is 2 or 3, or a $C_{1-3}$ alkoxylate when n is 3 or 4.

According to any embodiment of the invention, and independently of the specific aspects, said metal salt is selected amongst a salt of formula
- $(Zn^{2+})(X^-)_{2-m}(Y^-)_m$, wherein m, $X^-$ and $Y^-$ have the meaning indicated above, in particular m is 0;
- $(M^{3+})(X^-)_{3-m}(Y^-)_m$, wherein m, $X^-$ and $Y^-$ have the meaning indicated above and M is Al or Fe, in particular m is 0 or 1;
- $(Sn^{4+})(Cl^-)_{4-m}(R^5O^-)_m$ wherein m has the meaning indicated above, $R^5$ representing $C_{1-3}$ alkyl group, in particular m is 0 or 1.

According to any embodiment of the invention, said metal salt is a salt of formula:
- $(Zn^{2+})(X^-)_{2-m}(Y^-)_m$, wherein m, $X^-$ and $Y^-$ have the meaning indicated above;
- $(M^{3+})(X^-)_3$, wherein m, $X^{--}$ has the meaning indicated above and M is Al or Fe;
- $(Sn^{4+})(Cl^-)_4$.

According to any embodiment of the invention, and independently of the specific aspects, said metal salt is one wherein n is 2 or 3.

The metal salt can be added to the reaction medium as a preformed salt or generated in situ, for example as described in the Examples e.g. by the reaction of a carboxylate salt (for example $Zn(AcO)_2$) with $ClSi(R^b)_3$ or $R^bCOCl$.

Said Lewis acid may be also an alkyl aluminum chloride. According to any embodiment of the invention, and independently of the specific aspects, said alkyl aluminum chloride is of formula $Al(R^4)_aCl_{3-a}$, a representing 1 or 2 and $R^4$ representing $C_{1-4}$ alkyl or alkoxide group. According to any embodiment of the invention, and independently of the specific aspects, said alkyl aluminum chloride is selected amongst the compounds of formula $Al(R^4)_aCl_{3-a}$, a representing 1 or 2 and $R^4$ representing a $C_{1-3}$ alkyl group. According to any embodiment of the invention, said alkyl aluminum chloride is a compound wherein a represents 1 and $R^4$ represents a $C_{1-3}$ alkyl group, such as $EtAlCl_2$ or $Me_2AlCl$.

Said Lewis acid may be also a boron derivative of formula $BZ_3$. According to any embodiment of the invention, and independently of the specific aspects, said boron derivative is of formula $BZ_3$, wherein Z represents a fluoride or a phenyl group optionally substituted, and anyone of its adduct with a $C_2$-$C_8$ ether or a $C_1$-$C_6$ carboxylic acid. According to any embodiment of the invention, and independently of the specific aspects, said boron derivative is $BF_3$, and anyone of its adduct with a $C_4$-$C_6$ ether or a $C_1$-$C_3$ carboxylic acid, such as $BF_3^-(EtOEt)_{1-2}$ or $BF_3^-(AcOH)_{1-2}$.

According to any embodiment of the invention, said Lewis acid is selected amongst $Me_2AlCl$, $BF_3^-(HOOCMe)_{1-2}$, $(Zn^{2+})(X^-)_2$, $X^-$ being as defined above and in particular $Br^-$, $I^-$ or $Cl^-$, $FeCl_3$, $SnCl_4$, $Al(OTf)_3$.

Optionally, to said process of the invention, it can be also added an additive. Said additive accelerates the reaction and/or provides better yield of the desired product. According to any one of the above embodiments of the invention, said additive is amongst the group consisting of the compounds of formula $R^bCOCl$, $ClSiR^b_3$, $R^bCOOR^c$ or $(R^bCOO)_2R^d$, $R^b$ representing a $C_{1-8}$, or even $C_{1-4}$, alkyl group or a phenyl group optionally substituted by one or two $C_{1-4}$ alkyl or alkoxyl group, and $R^c$ representing a Li, Na, or K cation or a $R^bCO$ acyl group, and $R^d$ representing a Mg or Ca cation.

According to any one of the above embodiments of the invention, said additive, as non limiting example, can be $ClSiMe_3$, MeCOCl, AcOK or AcOAc.

In particular, when the Lewis acid is a metal salt as defined above, then it is most advantageous to use an additive of the silyl or acyl chloride type. Similarly, when the Lewis acid is of the alkyl aluminum chloride type or a boron derivative as described above, then it is most advantageous to use an additive of the alkali carboxylate or of the carboxylic anhydride type.

It goes without saying, as a person skilled in the art knows, that the addition of said additive can be done in one-pot (e.g. together with the catalyst or subsequently to the catalyst, in the same reaction medium) or in a kind of a two pot process (e.g. treating compounds (II) and (III) together with the catalyst and after a purification of the product thus obtained performing a treatment of said compound with the additive in a different reaction medium).

This second option (two-pot treatment) is particularly interesting in the case the Lewis acid is an alkyl aluminum chloride, since surprisingly we found that, in addition to the desired compound (I), an important product of the treatment with the Lewis acid can be a compound of formula

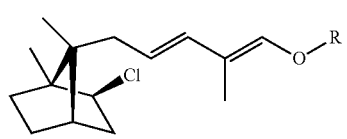

(I'')

in the form of any one of its stereoisomers or mixture thereof, and wherein R is as defined above;
and that said compound (I'') can be converted into the desired product (I), by adding an additive such as an alkali or alkaline-earth carboxylate or a carboxylic anhydride, preferably an alkali carboxylate as defined for the additive. Said compound (I'') is novel, and therefore as intermediate of compound (I) is also another aspect of the present invention.

The Lewis acid can be added to the reaction medium in a large range of concentrations. As non-limiting examples, one can cite $AlX_3$ or a transition metal salt, as described above, concentrations ranging from about 0.01 to 0.30 molar equivalents, relative to the molar amount of the starting compound (III), preferably comprised between about 0.001 and 0.15 molar equivalents. As non-limiting examples, one can cite alkyl aluminum chloride or a boron derivative, as described above, concentrations ranging from about 0.5 to 2.00 molar equivalents, relative to the molar amount of the starting compound (III), preferably comprised between about 0.7 and 1.3 molar equivalents.

It goes without saying that the optimum concentration of the salt will depend on the nature of the latter and on the desired reaction time, as well as the presence of an additive or not.

The additive can be added to the reaction medium in a large range of concentrations. As non-limiting examples, one can cite additive concentrations ranging from 10 to 250%, relative to the weight of the Lewis acid. Preferably, the additive concentration will be comprised between 10 and 120%, relative to the weight of the Lewis acid.

The process for the preparation of a compound (I), according to the invention, can be carried out under a number of various reaction conditions, provided that they are compatible with the reagents and the reactivity of the salt and additive. A person skilled in the art is able to select the most appropriate ones in view of its own needs. According to any embodiment of the invention, and independently of the specific aspects, one may cite as non limiting examples the following conditions, independent from each other or associated in any combination:

a reaction temperature comprised between −78° C. and 150° C., preferably between 0° C. and 60° C.; of course a person skilled in the art is also able to select the preferred temperature as a function of the melting and boiling point of the starting and final products and/or an eventual solvent;

the transformation of (II) into (I), in any of its embodiments, can be carried out in absence or in the presence of solvent; non-limiting examples of such a solvent are $C_{2-10}$ esters, $C_{1-6}$ chlorinated solvents and mixtures thereof. More preferably, the solvent is 1,2-dichloroethane or dichloromethane.

According to any embodiment of the invention, and independently of the specific aspects, the compounds (I), (I''), or (II) can be in the form of any one of its stereoisomers or mixtures thereof. For the sake of clarity by the term stereoisomer it is intended any diastereomer, enantiomer, racemate or carbon-carbon double bond isomer of configuration E or Z.

According to a particular embodiment of the invention, compound (I) is in the form of a mixture of stereoisomers comprising more than 50% (w/w) of the (1SR,2RS,4RS) stereoisomer, i.e. a compound having the relative exo configuration as shown in formula (I-A)

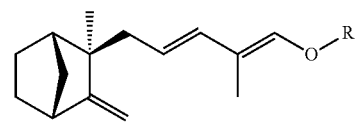

(I-A)

wherein R has the meaning indicated above in formula (I).

According to a particular embodiment of the invention, compound (I) is in the form of a mixture of stereoisomers comprising more than 50% (w/w) of the (1 S,2R,4R) stereoisomer, i.e. a compound having the absolute configuration as shown in formula (I-B)

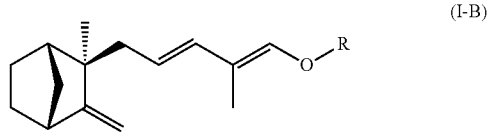

(I-B)

wherein R has the meaning indicated above in formula (I).

It is understood that, in any of the above or below embodiments, the starting material to prepare (e.g. (II) and (I")) or the product obtained from (e.g. see below (IV) and β-santalol) said compound (I) may have, and preferably does have, the same stereo configuration. By way of examples. one may cite the following reaction scheme:

Scheme 1:

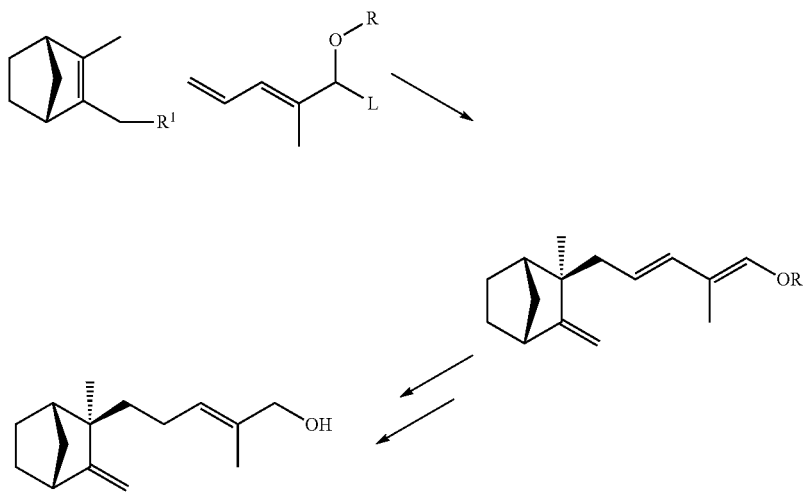

the stereo configuration being relative or absolute. So the present invention allows a three step process for β-santalol from e.g. santene.

A further object of the present invention is a process for the preparation of β-santalol, or its derivatives such as β-santalal, β-santalyl benzoate, β-santalyl butyrate, β-santalyl iso-butyrate, β-santalyl propionate, comprising a step as defined above. It is understood that a person skilled in the art knows how to perform said process using compound (I) obtained according to the invention's process.

The transformation of compound (I) into β-santalol can be performed in many different ways, which are well known by a person skilled in the art. Practical examples are provided in Examples herein below.

However, as non-limiting example, one of the most direct manners to transform the compound (I) into β-santalol comprises the following reactions:

a) reducing the dienol derivative (I) into a compound (IV)

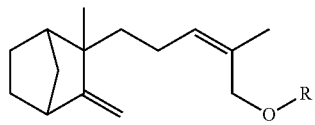

(IV)

in the form of any one of its stereoisomers or mixtures thereof, and wherein R has the same meaning as in formula (I);

b) converting said compound (IV) into the β-santalol.

Steps a) and b) can be performed according to standard methods well known by a person skilled in the art.

For instance, one may cite the following method for each step:

step a): according to Shibasaki et al., in *J.Org.Chem.*, 1988, 53, 1227 (where is reported the [1,4] hydrogenation of a dienol acetate derivative) or according to WO 08/120175 or WO 09/141781; and step b): see WO 09/141781.

An example of such procedure is provided in the Examples herein below.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 400 MHz or 125 MHz machine for $^1H$ or $^{13}C$ respectively, the chemical shifts δ are indicated in ppm with respect to TMS as standard, the coupling constants J are expressed in Hz. Santene: 2,3-dimethylbicyclo[2.2.1]hept-2-ene (II, R=H) was prepared according to *Chem. Ber.*, 1955, 88, 407. 2-methyl pentadienal could be prepared according to *J. Chem.Soc. Perkin Trans.* 1, 1986, 1203 or *Synth. Commun.*, 1985, 15, 371 or according to the procedure described below.

Example 1

Preparation of Compounds of Formula (III)

Preparation of (E)-ethyl 2-methylpenta-2,4-dienoate

Sodium ethoxide solution (21% in ethanol, 33.3 ml, cat.) was added to a solution of ethyl 2-methylpenta-3,4-dienoate (Bedoukian, 125.0 g, 890 mmol) in anhydrous ethanol (350 ml) and stirred at ambient temperature for 12 hours. The solution was concentrated in vacuo and the residue partitioned between ether and saturated $NH_4Cl$ solution. The aqueous phase was re-extracted twice with ether, then the combined organic phase washed with $NH_4Cl$ and then brine, dried over $Na_2SO_4$, filtered and the solvents removed in vacuo to yield the crude ester, 125.8 g as an orange oil which was used directly in the next step without further purification.

$^{13}C$ NMR: 168.4 (C), 138.2 (CH), 132.3 (CH), 128.2 (C), 124.0 ($CH_2$), 60.6 ($CH_2$), 14.3 ($CH_3$), 12.7 ($CH_3$)

Preparation of (E)-2-methylpenta-2,4-dien-1-ol $LiAlH_4$ (14.8 g, 389 mmol) was suspended in anhydrous ether (500 ml) and a solution of the ester (50.0 g, 357 mmol) in anhydrous ether (250 ml) was added slowly dropwise at such a rate as to maintain a gentle reflux. Following the addition the suspension was stirred at ambient temperature for a further 30 minutes then cooled to 0° C. in an ice bath. Distilled water (15 ml) was added extremely cautiously dropwise followed by 15% NaOH solution (15 ml) extremely cautiously followed by distilled water (45 ml). The white suspension was vigorously stirred at ambient temperature for 30 minutes then $Na_2SO_4$ was added and the suspension stirred for a further 30 minutes then filtered, the precipitate washed well with ether. The solvents were removed in vacuo to yield the crude alcohol, which was further purified by bulb to bulb distillation (0.09 mbar at 145° C.) to give the pure alcohol, 32.0 g.

$^{13}C$ NMR: 137.8 (C), 132.6 (CH), 125.4 (CH), 117.0 ($CH_2$), 68.2 ($CH_2$), 14.1 ($CH_3$)

Preparation of (E)-2-methylpenta-2,4-dienal

Manganese dioxide (45 g, 523 mmol) was added in one portion to a vigorously stirred solution of the alcohol (10.0 g, 102 mmol) in $CH_2Cl_2$ (200 ml) at ambient temperature. After 30 minutes a further portion of manganese dioxide (45 g, 523 mmol) was added in one portion followed by a further portion of 15 g. The suspension was stirred for a further 30 minutes at ambient temperature, then filtered through a 6 cm plug of celite. The solid was washed with $CH_2Cl_2$. The combined washings were dried over $Na_2SO_4$ then filtered and used directly in the next step. A small portion was evaporated to dryness in vacuo (300 mbar) to yield the aldehyde.

$^{13}C$ NMR: ($CD_2Cl_2$) 195.2 (CH), 148.6 (CH), 138.4 (C), 132.0 (CH), 126.3 ($CH_2$), 9.6 ($CH_3$)

General Procedure for the Preparation of the (E)-2-methylpenta-2,4-diene-1,1-diyl-diesters The anhydride (0.306 mol) was added to a stirred solution of the freshly prepared 2-methylpentadienal (9.8 g, 0.102 mol) in $CH_2Cl_2$ (100 ml) and the solution cooled to 0° C. $FeCl_3$ anhydrous, (2% w/w, 0.15 g) was added in one portion. The solution was stirred at 0° C. for 5 hours, then poured into a mixture of ether and saturated $NaHCO_3$ and stirred overnight at ambient temperature. Re-extracted twice with ether, then washed combined organic phase with saturated $NaHCO_3$ (2×), saturated $NH_4Cl$, brine, then dried over $Na_2SO_4$, filtered and the solvents removed in vacuo to yield the crude diesters. Further purification by bulb to bulb distillation gave the pure diesters.

1. Preparation of (E)-2-methylpenta-2,4-diene-1,1-diyl diacetate

Bulb to bulb distillation at 0.6 mbar at 100° C. gave the desired diacetate, 6.5 g, 32%.

$^{13}C$ NMR: 168.6 (C), 131.5 (CH), 130.9 (C), 130.7 (CH), 120.7 ($CH_2$), 92.4 (CH), 20.8 ($CH_3$), 11.3 ($CH_3$)

2. Preparation of (E)-2-methylpenta-2,4-diene-1,1-diyl propionate

Bulb to bulb distillation at 0.1 mbar at 120° C. gave the desired dipropionate, 1.8 g, 16%.

$^{13}C$ NMR: 172.2 (C), 131.5 (CH), 131.1 (C), 130.5 (CH), 120.5 ($CH_2$), 92.3 (CH), 27.4 ($CH_2$), 11.3 ($CH_3$), 8.8 ($CH_3$)

3. Preparation of (E)-2-methylpenta-2,4-diene-1,1-diyl bis(2-methylpropanoate)

Bulb to bulb distillation at 0.1 mbar at 125° C. gave the desired diisobutyrate, 6.1 g, 48%.

$^{13}C$ NMR: 174.7 (C), 131.6 (CH), 131.2 (C), 130.3 (CH), 120.4 ($CH_2$), 92.1 (CH), 34.0 (CH), 18.7, 18.6 ($CH_3$), 11.3 ($CH_3$)

Example 2

Preparation of (1E,3E)-2-methyl-5-((1SR,2RS,4RS)-2-methyl-3-methylenebicyclo[2.2.1]heptan-2-yl)penta-1,3-dien-1-yl acetate Use of $ZnBr_2$ $ZnBr_2$ (155 mg, 0.7 mmol) was added to stirred dienyl diacetate (2.5 g, 12.5 mmol) at ambient temperature. The suspension was stirred for 15 minutes at ambient temperature, then a solution of santene (1.23 g, 10 mmol) in $CH_2Cl_2$ (3 ml) was added slowly dropwise. The brown suspension was stirred at ambient temperature for a further 3 hours, then diluted with ethyl acetate, and $NaHCO_3$, re-extracted with ethyl acetate, washed combined organic phase with $NaHCO_3$, dried over $MgSO_4$, filtered and the solvent removed in vacuo to yield the crude dienyl acetate, 3.11 g as a yellow oil.

Further purification by bulb to bulb distillation 0.12 mbar at 150-165° C., gave the desired dienyl acetate, 2.08 g. (12:1, exo:endo, yield=80%).

$^{13}C$ NMR: 167.9 (C), 165.4 (C), 134.4 (CH), 130.7 (CH), 126.8 (CH), 120.7 (C), 100.0 ($CH_2$), 46.9 (CH), 45.3 (C), 45.0 (CH), 44.5 ($CH_2$), 37.0 ($CH_2$), 29.7 ($CH_2$), 23.7 ($CH_2$), 23.0 ($CH_3$), 20.8 ($CH_3$), 10.4 ($CH_3$)

Use of $ZnCl_2$ $ZnCl_2$ (20 mg, 5 mol %) was added to the dienyl diacetate (402 mg, 2 mmol) in $CH_2Cl_2$ (2 ml) and stirred for 5 minutes at ambient temperature. Santene (240 mg, 2 mmol) was then added dropwise. The mixture was stirred at ambient temperature for a further 3 hours. Diluted with ethyl acetate, then added $NaHCO_3$ stirred overnight at ambient temperature. Re-extracted with ethyl acetate, washed combined organic phase with $NaHCO_3$, filtered and the solvents removed in vacuo to yield the crude dienyl acetate, 0.48 g. Further purification by bulb to bulb at 1 mbar 165° C. gave the dienyl acetate, 0.27 g, yield=50%. (20:1, exo:endo). Spectroscopically identical to that prepared above.

Use of $ZnI_2$ and In Situ Generation of the Compound (III)

$ZnI_2$ (0.1 mmol, 3 mol %, 0.033 g) was added to a solution of dienal (0.35 g, 3.5 mmol) and santene (0.52 g, 4 mmol) in $CH_2Cl_2$ (3 ml) at ambient temperature. Acetic anhydride (0.5 g, 5 mmol) was added slowly dropwise over 10 minutes. Added $ZnCl_2$ (0.025 g, 1 mol %) and the solution stirred at ambient temperature for 48 hours. Then diluted with ethyl acetate then $NaHCO_3$, re-extracted with ethyl acetate, washed combined organic phase with $NaHCO_3$, dried over $MgSO_4$, filtered and the solvents removed in vacuo to yield the crude dienyl acetate, 1.0 g as a dark yellow oil.

Further purification bulb to bulb distillation 0.45 mbar at 175° C. gave the dienyl acetate, 0.46 g, yield=48% (30:1, exo:endo). Spectroscopically identical to that prepared previously.

Example 3

Preparation of (1E,3E)-2-methyl-5-((1SR,2RS,4RS)-2-methyl-3-methylenebicyclo[2.2.1]heptan-2-yl)penta-1,3-dien-1-yl acetate General Procedure:

The Lewis acid (5-10 mol %) was added to a stirred mixture of santene (122 mg, 1 mmol) and the allylidene diacetate (180 mg, 1.1 mmol) in dichloromethane (1 ml) cooled to 0° C. After 30 minutes at 0° C. the solution was allowed to warm to ambient temperature and stirred for a further 2-4 hours at ambient temperature. Conversion analyzed by GC.

TABLE 1

Reaction catalysed by various Lewis acids

| Lewis acid (10 mol % if not specified) | % GC[1] exo | % GC[1] endo | % GC[2] Compound (I") | Ratio exo:endo |
|---|---|---|---|---|
| 0.9 eq $EtAlCl_2$ | 47 | 4 | 14 | 92:8 |
| 0.9 eq $Et_2AlCl$ | 39 | 2 | 24 | 95:5 |
| 0.9 eq $MeAlCl_2$ | 38 | 3 | 5.5 | 93:7 |
| 0.9 eq $Me_2AlCl$ | 53 | 3 | 12 | 95:5 |
| $BF_3 \cdot Et_2O$ | 68 | 9 | | 88:12 |
| $BF_3 \cdot HOAc$ | 74 | 10 | | 88:12 |
| $Zn(OTs)_2$ + 2 eq. TMS-Cl | 42 | 4 | 31 | 90:10 |
| $Zn(acac)_2$ + 2 eq. AcCl | 13 | 6 | 31 | 68:32 |
| $Zn(acac)_2$ + 2 eq. TMS-Cl | 56 | 11 | 12 | 84:16 |
| $Zn(TFA)_2$ + 2 eq. AcCl | 13 | 5 | 41 | 72.28 |
| $Zn(TFA)_2$ + 2 eq. TMS-Cl | 59 | 10 | 13 | 85:15 |
| Zn(oxalate) + 2 eq. AcCl | 11 | 4 | 49 | 76:24 |
| Zn(oxalate) + 2 eq. TMS-Cl | 18 | 2 | 45 | 89:11 |
| $Zn(3,5-ditertBu\ salicylate)_2$ + 2 eq. AcCl | 12 | 2 | 64 | 86:14 |
| $Zn(3,5-ditertBu\ salicylate)_2$ + 2 eq. TMS-Cl | 53 | 8 | 21 | 87:13 |
| $FeCl_3$ | 77 | 2 | | 97:3 |
| $Al(BF_4)_3$* | 40 | 13 | | 75/25 |
| $Al(OTf)_3$ | 72 | 1 | | 98.5:1.5 |
| $Al(OPr^i)_3$ + 2 eq. AcCl | 11 | 1 | | 92:8 |
| $Ce(OTf)_3$* | 53 | 1 | | 98:2 |
| $Sc(OTf)_3$* | 22 | 10 | | 75:25 |
| $La(OTf)_3$* | 26 | 0.8 | | 98:2 |
| $PrOZrCl_3$ | 18 | 0.4 | | 98:2 |
| $SnCl_4$ | 71 | 2 | | 97:3 |
| $Cu(OTf)_2$ | 30 | 15 | | 77:33 |
| $Mg(OTf)_2$ | 58 | 3 | | 94:6 |
| $Cu(BF_4)_2$* | 57 | 8 | | 88:12 |

*= 5 mol %; acac = acetylacetonate; TFA = trifluoroacetic acid; OTs = paratoluenesulfonate; OTf = trifluoromethylsulfonate
[1]= yield observed by GC of the mentioned isomer of compound (I)
[2]= yield observed by GC of the mentioned compound

Example 4

Preparation of (1E,3E)-2-methyl-5-((1SR,2RS,4RS)-2-methyl-3-methylenebicyclo[2.2.1]heptan-2-yl)penta-1,3-dien-1-yl carboxylate General Procedure:

$Al(OTf)_3$ (0.024 g, 1 mol %) was added in one portion to a stirred mixture of the santene (0.61 g, 5 mmol) and the 2-methylpenta-2,4-diene-1,1-diyl ester (5 mmol) at ambient temperature. After a further 60 minutes poured into saturated sodium bicarbonate and ether. Re-extracted with ether, washed combined organic phase with ammonium chloride then brine, dried over sodium sulfate, filtered and the solvents removed in vacuo to yield the crude dienyl ester. Further purification by bulb to bulb distillation gave the pure dienyl ester as a mixture of exo and endo isomers.

1. (1E,3E)-2-methyl-5-((1SR,2RS,4RS)-2-methyl-3-methylenebicyclo[2.2.1]heptan-2-yl)penta-1,3-dien-1-yl propionate 5 mmol scale, bulb to bulb distillation 175° C. at 0.6 mbar gave the dienyl propionate, 0.99 g, yield=72%. (Exo:endo=50/1).

$^{13}$C NMR: 171.3 (C), 165.5 (C), 134.4 (CH), 130.7 (CH), 126.8 (CH), 120.6 (C), 100.0 ($CH_2$), 46.9 (CH), 45.3 (C), 45.0 (CH), 44.5 ($CH_2$), 37.0 ($CH_2$), 29.7 ($CH_2$), 23.7 ($CH_2$), 27.5 ($CH_3$), 23.0 ($CH_3$), 10.4 ($CH_3$), 9.0 ($CH_3$)

2. (1E,3E)-2-methyl-5-((1SR,2RS,4RS)-2-methyl-3-methylenebicyclo[2.2.1]heptan-2-yl)penta-1,3-dien-1-yl isobutyrate 5 mmol scale, bulb to bulb distillation 175° C. at 0.6 mbar gave the dienyl isobutyrate, 1.0 g, yield=70%. (Exo:endo=50/1).

$^{13}$C NMR: 173.9 (C), 165.4 (C), 134.5 (CH), 130.7 (CH), 126.8 (CH), 120.7 (C), 100.0 ($CH_2$), 46.9 (CH), 45.3 (C), 45.0 (CH), 44.5 ($CH_2$), 37.0 ($CH_2$), 29.7 ($CH_2$), 23.7 ($CH_2$), 34.0 (CH), 18.8, 18.3 ($CH_3$), 23.0 ($CH_3$), 10.4 ($CH_3$)

Example 5

Preparation of (1E,3E)-2-methyl-5-((1SR,2RS,4RS)-2-methyl-3-methylenebicyclo[2.2.1]heptan-2-yl)penta-1,3-dien-1-yl acetate via compound of formula (I")

(1E,3E)-5-((1SR,2SR,4SR,7RS)-2-chloro-1,7-dimethylbicyclo[2.2.1]hetan-7-yl)-2-methylpenta-1,3-dien-1-yl acetate (I")

Diethyl aluminum chloride (1.0 M in hexanes, 7.2 ml, 7.2 mmol) was added dropwise over 15 minutes to a stirred solution of Santene (978 mg, 8 mmol) and the dienyl diacetate (1982 mg, 10 mmol) in CH$_2$Cl$_2$ (8 ml) cooled to 0° C. Stirred at 0° C. for further 90 minutes, then poured into ice and saturated NaHCO$_3$, re-extracted with ether, washed combined organic phase with NaHCO$_3$, dried over Na$_2$SO$_4$, filtered and the solvents removed in vacuo to yield the crude dienyl acetate, 1.7 g as a yellow oil.

Further purification by bulb to bulb distillation 0.12 mbar at 180° C., gave the desired dienyl acetate, 0.82 g. Identical to that prepared above. The residue contained the desired chloro dienyl acetate, 0.15 g, (yield=6%).

$^{13}$C NMR: 167.9 (C), 134.2 (CH), 130.1 (CH), 127.2 (CH), 120.7 (C), 68.2 (CH), 50.8 (C), 50.6 (C), 43.3 (CH), 42.1 (CH$_2$), 36.7 (CH$_2$), 36.4 (CH$_2$), 26.8 (CH$_2$), 20.8 (CH$_3$), 16.9 (CH$_3$), 13.5 (CH$_3$), 10.4 (CH$_3$)

(1E,3E)-2-methyl-5-((1SR,2 RS,4RS)-2-methyl-3-methylenebicyclo[2.2.1]heptan-2-yl)penta-1,3-dien-1-yl acetate Treatment of the chloro dienyl acetate obtained above (150 mg) and potassium acetate (250 mg) at 150° C. gave the desired dienyl acetate spectroscopically identical to that prepared previously (yield=quantitative).

Example 6

Preparation of β-Santalol (Z)-2-methyl-5-((1SR,2 RS,4RS)-2-methyl-3-methylenebicyclo[2.2.1]heptan-2-yl)pent-2-en-1-yl isobutyrate (compound of formula (IV))

The freshly distilled dienyl isobutyrate (1.0 g, 3.5 mmol) and maleic acid (25 mg, 2.2 mol %) were placed in a s/s autoclave and the catalyst RuCp*COD.BF$_4$, (30 mg, 2 mol %) was then added. Acetone (2 ml, degassed with ultrasound and argon bubbling, stored under argon) was added last and the mixture sealed, evacuated then purged with hydrogen 5 times. The suspension was stirred under an atmosphere of hydrogen 5 bars at 60° C. for 12 hours. Then filtered through a plug of silica (5 cm) with ethyl acetate as eluent, then the solvents removed in vacuo to yield the crude product. Further purification by column chromatography cartridge (80 g) with 1:99 ethyl acetate:cyclohexane as eluent gave the pure isobutyrate, 0.9 g which was further purified by bulb to bulb distillation 175° C. at 0.6 mbar to give the pure desired product, 0.71 g, yield=72% as a mixture of exo:endo, 50:1, (Z:E selectivity >98:2).

$^{13}$C NMR: 177.2 (C), 166.2 (C), 131.1 (CH), 129.7 (C), 99.7 (CH$_2$), 63.0 (CH$_2$), 46.8 (CH); 44.8 (C), 44.6 (CH), 41.2 (CH$_2$), 37.1 (CH$_2$), 34.1 (CH), 29.7 (CH$_2$), 23.7 (CH$_2$), 23.4 (CH$_2$), 22.6 (CH$_3$), 21.4 (CH$_3$), 19.0 (CH$_3$)

(Z)-2-methyl-5-((1SR,2 RS,4RS)-2-methyl-3-methylenebicyclo[2.2.1]heptan-2-yl)pent-2-en-1-ol (β-santalol)

The allylic acetate (1.25 g, 4.5 mmol) was dissolved in methanol (15 ml) and sodium methoxide (23% solution in methanol, 100 µl) was added and the solution was stirred for 1 hour. The majority of the methanol was removed in vacuo, then the residue was partioned between cyclohexane and water. Re-extracted with cyclohexane and then the combined organic phases washed with water, then NaHCO$_3$, dried over K$_2$CO$_3$ and MgSO$_4$, then filtered. The solvents were removed in vacuo to yield the crude β-santalol, 1.1 g. Further purification by bulb to bulb distillation 170° C. at 0.1 mbar gave a mixture of β-santalol and epi-β-santalol 96:4 (exo:endo), 0.9 g, yield=90% (Z:E selectivity >99:1).

$^{13}$C NMR: 166.2 (C), 133.9 (C), 129.0 (CH), 99.7 (CH$_2$), 61.6 (CH$_2$), 46.8 (CH), 44.7 (C), 44.6 (CH), 41.5 (CH$_2$), 37.1 (CH$_2$), 29.7 (CH$_2$), 23.7 (CH$_2$), 23.2 (CH$_2$), 22.6 (CH$_3$), 21.3 (CH$_3$)

What is claimed is:

1. A compound of formula

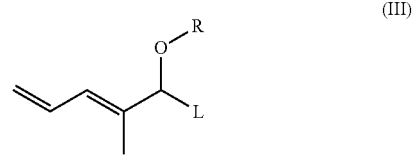

(III)

in the form of any one of its stereoisomers or mixtures thereof, wherein L represents a halogen atom or an OR group, wherein each R represents a C$_2$-C$_{10}$ group of formula COR$^a$ wherein R$^a$ is an alkyl or alkenyl group optionally comprising one or two ether functional groups or is a phenyl or benzyl group optionally substituted by one to three alkyl, alkoxyl, carboxyl, acyl, amino or nitro groups or halogen atoms.

2. A compound according to claim 1, wherein L represents an OR group.

3. A compound according to claim 1, wherein R represents a C$_{2-7}$ acyl group of formula COR$^a$ wherein R$^a$ is as defined in claim 1.

4. A compound according to claim 3, wherein L represents an OR group.

* * * * *